United States Patent
Musset et al.

(10) Patent No.: US 6,423,096 B1
(45) Date of Patent: Jul. 23, 2002

(54) KNEE PROSTHESIS FEMORAL IMPLANT AND ORTHOPAEDIC EQUIPMENT SET COMPRISING SUCH A FEMORAL IMPLANT

(75) Inventors: Thierry Musset, L'Amor Plage; Jacques Le Saout, L'Aber Wrach, both of (FR)

(73) Assignee: Depuy France, Villeurbanne (FR)

( * ) Notice: Subject to any disclaimer, the term of this patent is extended or adjusted under 35 U.S.C. 154(b) by 0 days.

(21) Appl. No.: 09/582,095
(22) PCT Filed: Dec. 10, 1998
(86) PCT No.: PCT/FR98/02692
§ 371 (c)(1), (2), (4) Date: Sep. 26, 2000
(87) PCT Pub. No.: WO99/32053
PCT Pub. Date: Jul. 1, 1999

(30) Foreign Application Priority Data

Dec. 22, 1997 (FR) .............................. 97 16271

(51) Int. Cl.$^7$ .................................................. A61F 2/38
(52) U.S. Cl. .................................................. 623/20.15
(58) Field of Search ........................... 623/20.15, 20.34, 623/20.36, 20.16, 20.18

(56) References Cited

U.S. PATENT DOCUMENTS

| | | |
|---|---|---|
| 5,133,760 A | 7/1992 | Petersen et al. |
| 5,152,796 A | 10/1992 | Slamin |
| 5,326,359 A | 7/1994 | Oudard |
| 5,405,395 A | 4/1995 | Coates |
| 5,776,200 A * | 7/1998 | Johnson et al. ............. 623/20 |
| 5,879,391 A * | 3/1999 | Slamin ....................... 623/20 |
| 6,071,311 A * | 6/2000 | O'Neil et al. .............. 623/20 |
| 6,162,255 A * | 12/2000 | Oyola ..................... 623/20.34 |
| 6,171,342 B1 * | 1/2001 | O'Neil et al. ........... 623/20.15 |

* cited by examiner

Primary Examiner—Bruce Snow
(74) Attorney, Agent, or Firm—Young & Thompson

(57) ABSTRACT

A knee prosthesis femoral implant includes two condyles integral with a throchlea and a centro-medullary block adapted to be fixed on a support base arranged between the condyles. The implant includes a wedge linking the base and the block. There is appropriate angular positioning of the wedge and the block both in a valgus front plane and in a sagittal plane relative to the reference front plane. The wedge has flat proximal and distal faces forming between them a predetermined angle ($\beta$) which, combined with an angle of inclination ($\alpha$) at the base surface receiving the wedge, enables, depending on the orientation of the wedge, two different femoral valgus values for each wedge. The wedge can also have different profiles in the sagittal plane. The invention enables a wide range of possibilities for adjusting the femoral valgus and for positioning the wedge in an antero-posterior plane relative to a reference plane, with a reduced number of wedges.

10 Claims, 10 Drawing Sheets

KNEE PROSTHESIS FEMORAL IMPLANT AND ORTHOPAEDIC EQUIPMENT SET COMPRISING SUCH A FEMORAL IMPLANT

BACKGROUND OF THE INVENTION

The present invention relates to a femoral implant of a knee prosthesis, comprising two condyles integral with a trochlea and a centro-medullary stem adapted to be fixed on a support base arranged between the condyles.

It is known that the centro-medullary stem of an implant must be oriented correctly in the frontal plane in order to respect the patient's femoral valgus angle, and, on the other hand, in the sagittal plane in order to be well positioned with respect to the inner wall of the trochlea, in order to obtain good primary securing of the implant, the stem having to be suitably placed with respect to the anterior cortex.

The femoral valgus angle is the angle located in the frontal plane between the anatomical axis of the femur and its mechanical taxis, this angle having a value generally between 3 and 11 degrees.

In summary, the centro-medullary stem must be oriented angularly so as to be able to satisfy three imperatives: preservation of the anterior cortex, good secondary securing in the centro-medullary canal, and preservation of the femoral valgus angle of the patient's knee.

In an attempt to attain these objectives, sets of stems have been proposed in particular having various orientations of femoral valgus angles and in the sagittal plane in order to correspond to a large number of anatomical possibilities. Such embodiments require virtually as many different parts as there are anatomical possibilities, therefore a very large number of parts, which renders the assembly very expensive and cumbersome.

Patent U.S. Pat. No. 5,152,796 and Patent EP-A-0 714 645 describe femoral implants comprising an intermediate piece forming a wedge element or "pre-stem", interposed between the support boss or base in one piece with the frontal plane, and presents a lower face inclined with respect to the surface of the base, which makes it possible to adapt it to the valgus angle of the femur, equally well for the right femur of for the left femur by turning through 180 degrees.

Furthermore, this same Patent EP 0 714 645 provides positioning a screw for securing the pre-stem in the immediate proximity of the trochlea, in the axis of the stem, which has the consequence of considerably restricting the femoro-patellar bearing surface for the patella.

In effect, the result of this proximity of the screw for securing the stem with respect to the trochlea is that the femoro-patellar zone of contact of the patella on the trochlea is necessarily interrupted at the level of the recess for passage of the screw. Consequently, when the patella passes beyond the corresponding interruption of its bearing surface, its bearing is reduced to two points instead of a line of contact. The consequence of this is an increase in the stresses on the patella, therefore wear of the polyethylene of the patella, which may be replaced prematurely. In the patent mentioned above, the line of contact is thus replaced by two points of contact after a flexion of only about 65 degrees.

The patent U.S. Pat. No. 5,405,395 discloses a femoral implant equipped with a pre-stem providing only one angular possibility for the centro-medullary stem, so that the surgeon must have a sufficient number of pre-stems available. Moreover, the line of contact of the patella with the femoro-patellar surface extends over an angle of flexion of considerably less than 90 degrees.

SUMMARY OF THE INVENTION

It is an object of the invention to propose a femoral implant arranged so as to satisfy the imperatives set forth hereinabove and in particular to provide the patella with an increased femoro-patellar sliding surface, employing a reduced number of parts compared to the embodiments of the prior art, producing a less expensive assembly of orthopaedic material which is more convenient for the surgeons to use.

According to the invention, the femoral implant for knee prosthesis comprises a pre-stem for connection between the base and the stem, and this pre-stem as well as the base are provided with means allowing an appropriate angular positioning of the pre-stem and of the stem, both in a frontal plane in valgus and in a sagittal plane with respect to a frontal reference plane; the implant also comprises means for securing four pre-stems offering a total of eight possibilities, including four possibilities of femoral valgus angles and four possibilities in the sagittal plane with respect to the frontal reference plane, which is the anterior plane parallel to the anterior face of the femur.

The surgeon thus has at his disposal an orthopaedic assembly constituted by a left femoral implant, a right femoral implant with their stems, and a set of a certain number of pre-stems, offering a wide range of possibilities adaptable to virtually all anatomical cases.

Finally, thanks to the offset positioning towards the condyles of the element for securing the pre-stem and the stem, the femoro-patellar zone of bearing of the patella may be considerably increased with respect to the prior art mentioned hereinabove, up to an angle of flexion close to 90 degrees. This results in a reduction in the stresses on the patella and therefore in the wear thereof.

Other features and advantages of the invention will emerge in the course of the following description, made with reference to the accompanying drawings which illustrate two embodiments of the invention without any limitation being implied.

Figure 4:
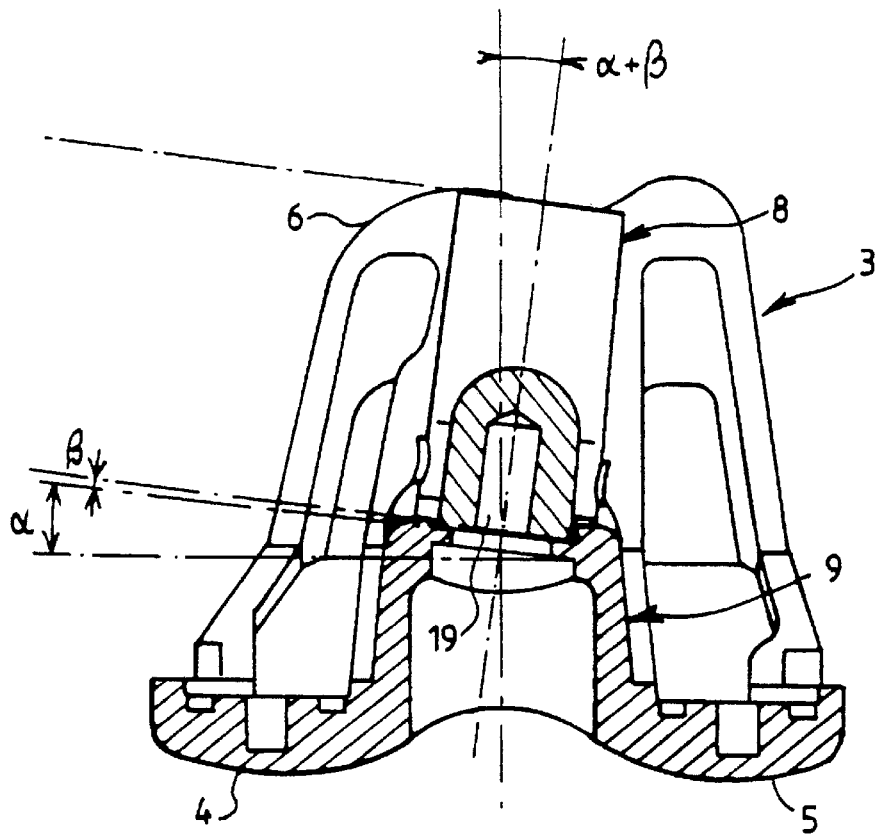
FIG. 4 is a view similar to FIG. 2 for femoral implant intended for a patient's right femur.
Figure 5:
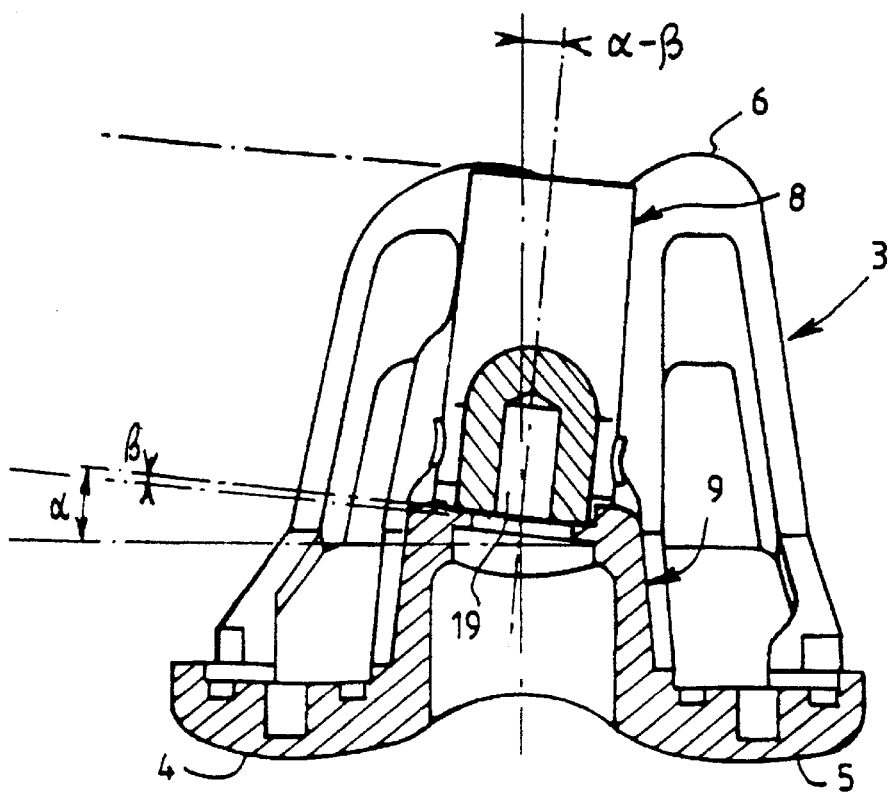
FIG. 5 is a view similar to FIG. 4, showing a second value of the valgus angle with another pre-stem.
Figure 4A:
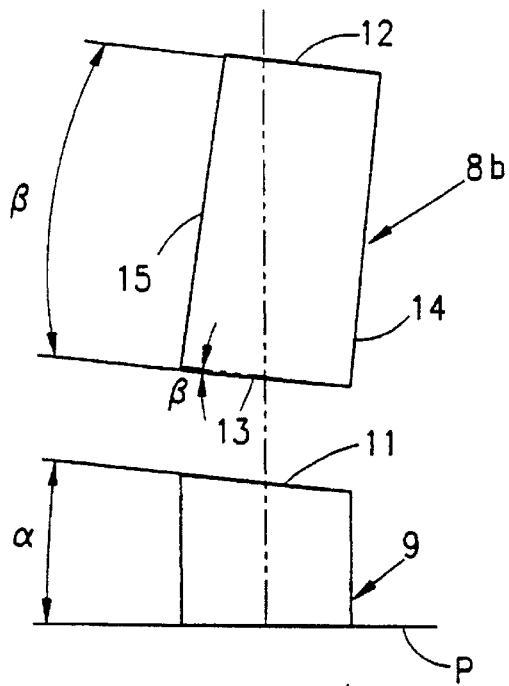
FIGS. 4A and 4B are similar to the diagrams of FIGS. 2A and 2B and illustrate the manner in which the pre-stem may be positioned on its base to obtain a femoral valgus angle according to FIG. 4.
Figure 4B:
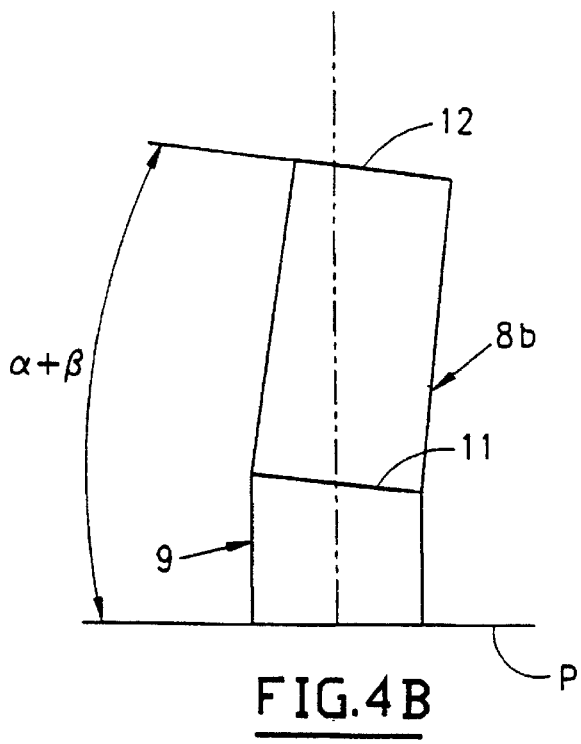
Figure 5A:
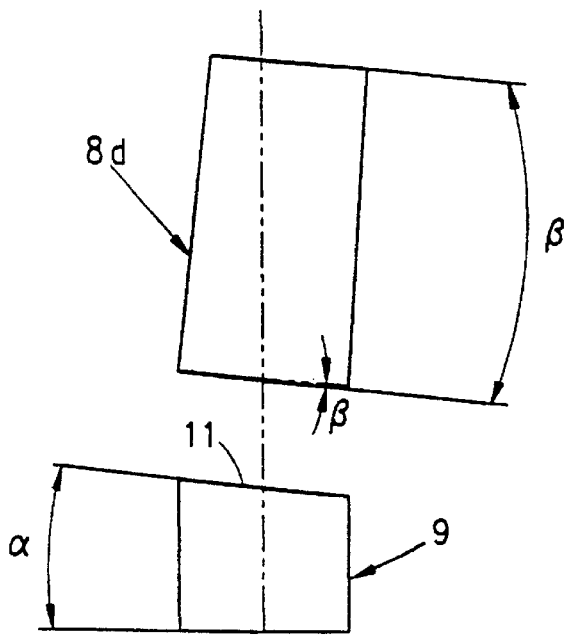

FIGS. 5A and SB are diagrams similar to FIGS. 4A and 4B showing the manner in which the pre-stem may be positioned on the base of the implant to obtain a femoral valgus angle according to FIG. 5.

Figure 6:
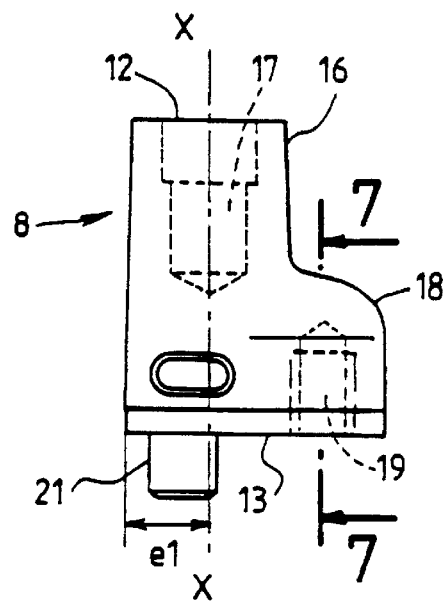

FIG. 6 is a view in side elevation of a first embodiment of the pre-stem equipping the implants of FIGS. 1 to 5.

Figure 7:
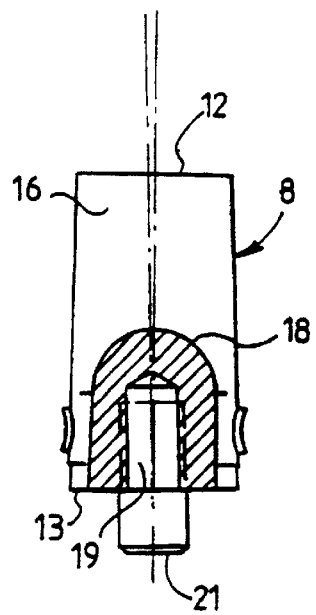

FIG. 7 is a view in section along 7/7 of FIG. 6.

Figure 8:
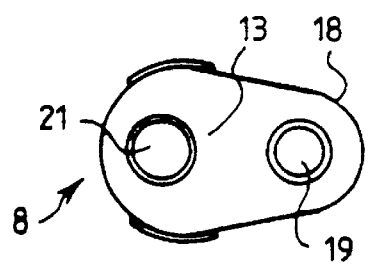

FIG. 8 is a view from underneath of the pre-stem of FIGS. 6 and 7.

Figure 9:
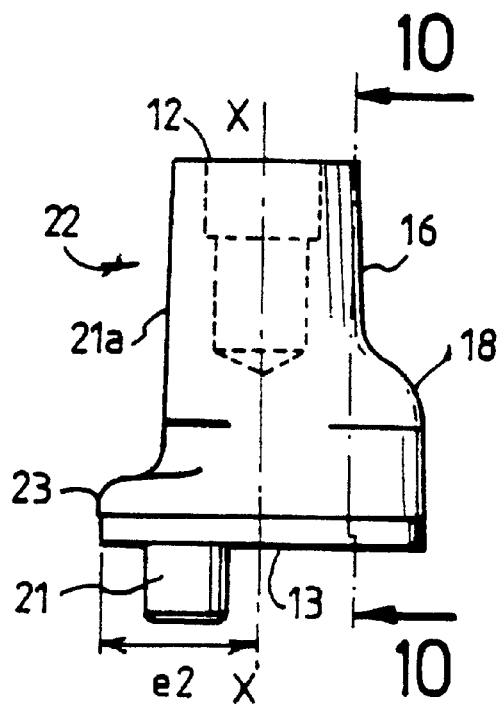

FIG. 9 is a view in side elevation of a second embodiment of the pre-stem adapted to equip the implants of FIGS. 1 to 5.

Figure 10:
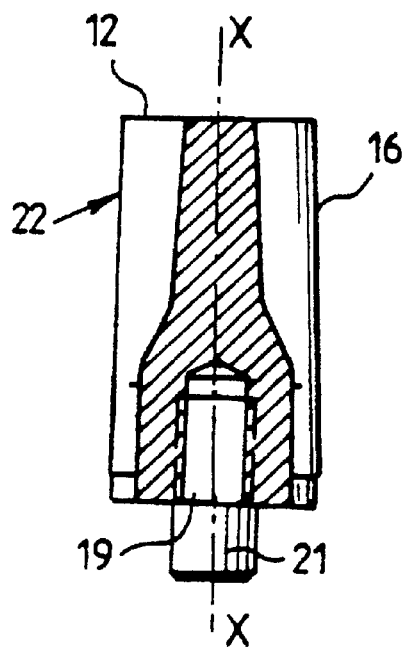

FIG. 10 is a view in section along 10/10 of FIG. 9.

Figure 11:
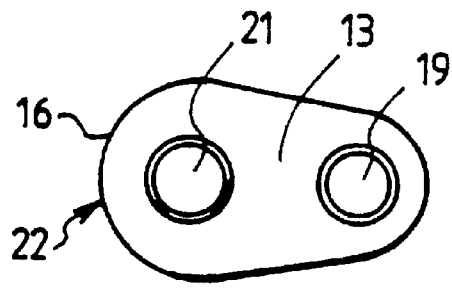

FIG. 11 is a view from underneath of the pre-stem of FIGS. 9 and 10.

Figure 12:
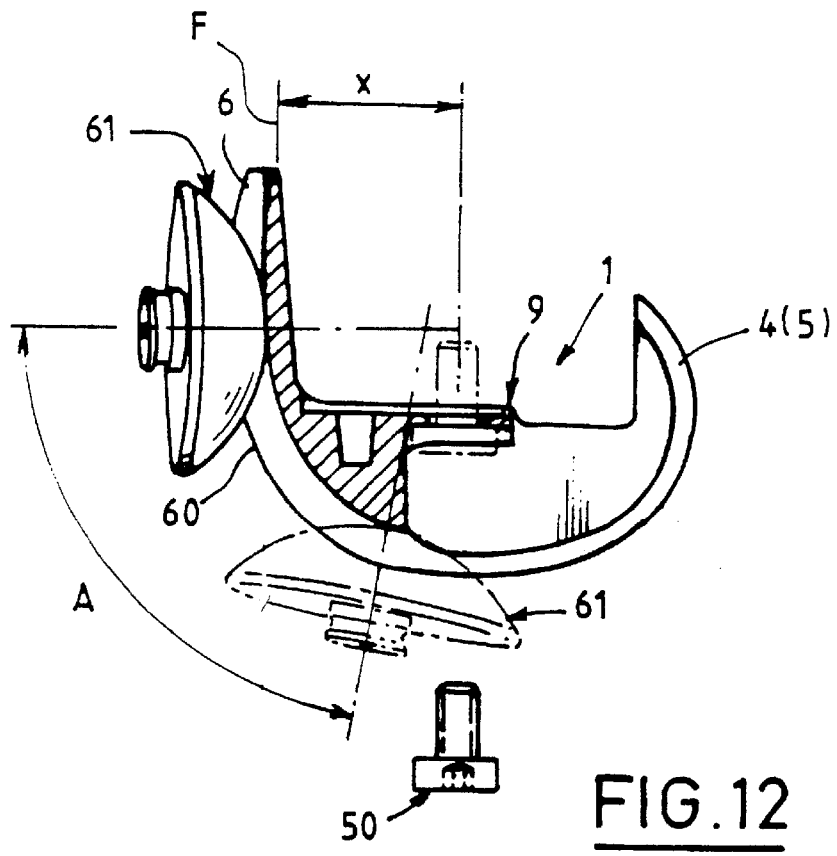

FIG. 12 is a view in elevation in a sagittal plane of the implant and its patella, shown in its two extreme positions of flexion on the trochlea.

Figure 13:
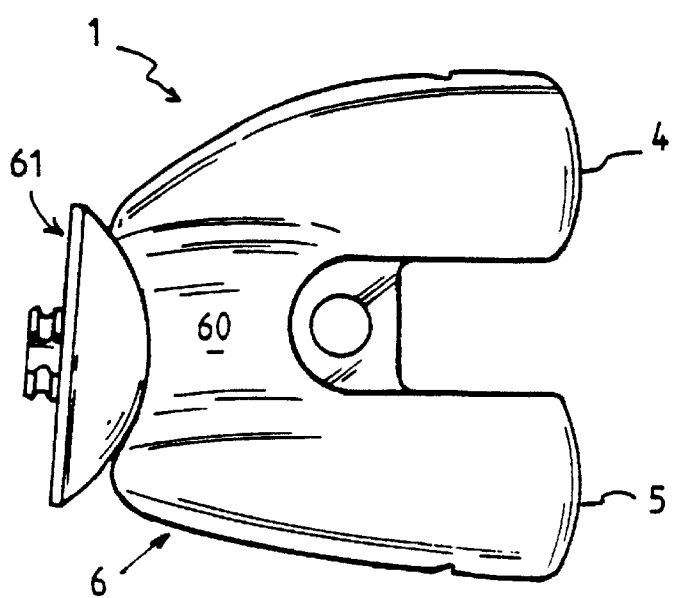

FIG. 13 is a view from underneath corresponding to FIG. 12.

Figure 14:
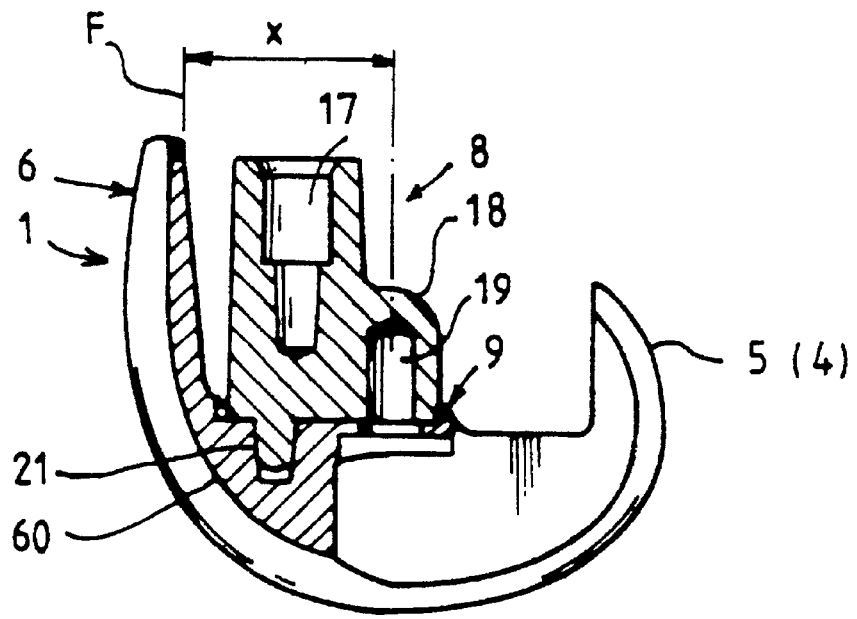
Figure 15:
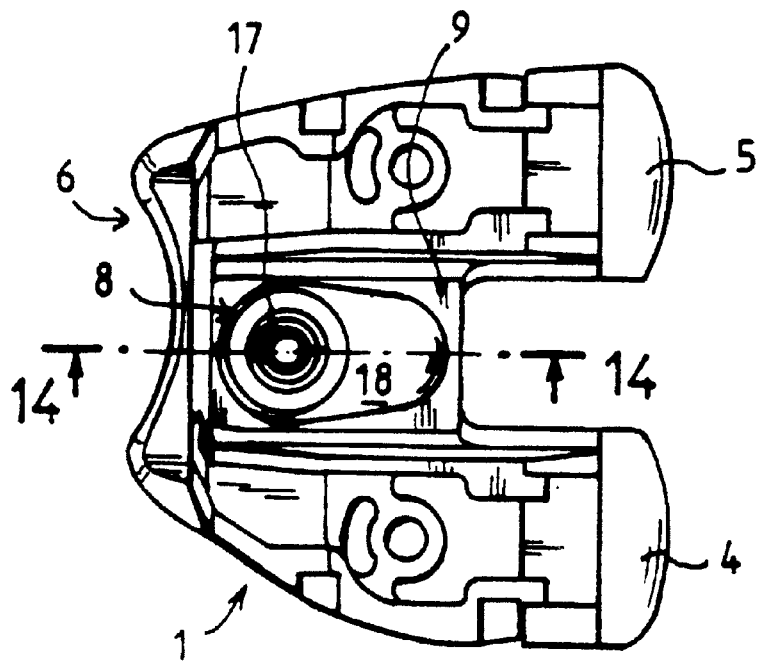

FIG. 14 is a view in section in a sagittal plane along 14—14 of FIG. 15 of an implant provided with a pre-stem according to the embodiment of FIG. 6.

FIG. 15 is a plan view corresponding to FIG. 14.

Figure 16:
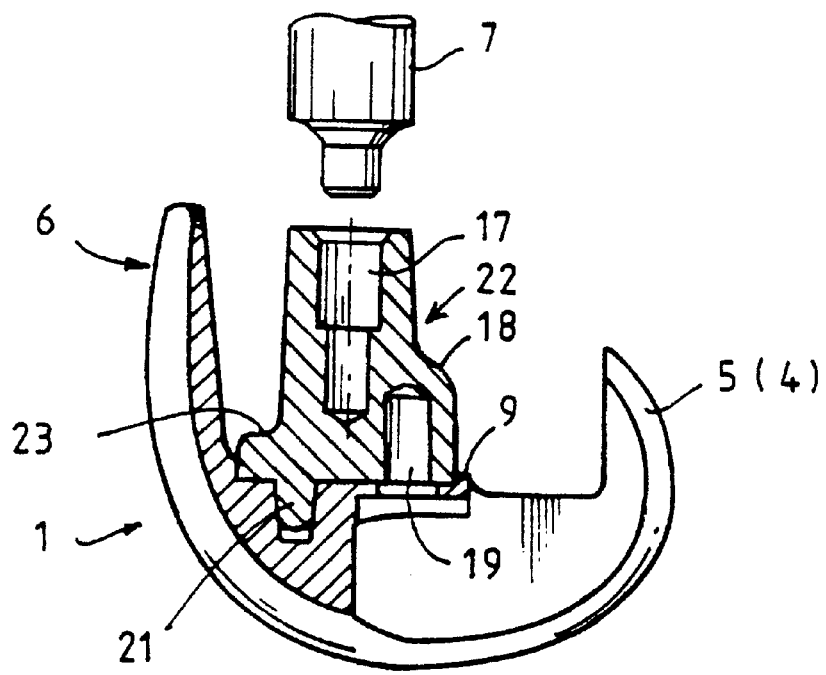
Figure 17:
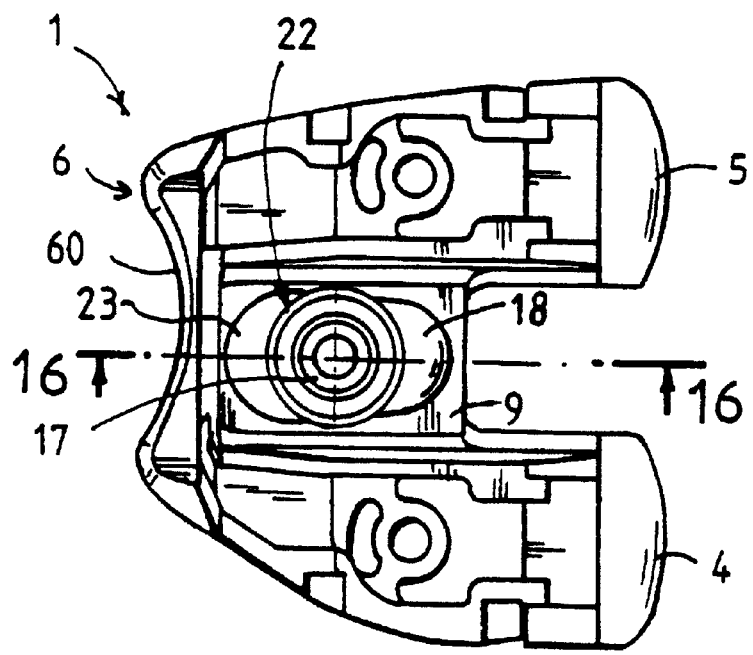

FIG. 16 is a view in section along 16—16 of FIG. 17 of an implant provided with a pre-stem according to the embodiment of FIG. 9.

FIG. 17 is a plan view corresponding to FIG. 16.

DETAILED DESCRIPTION OF THE PREFERRED EMBODIMENTS

Figure 1:
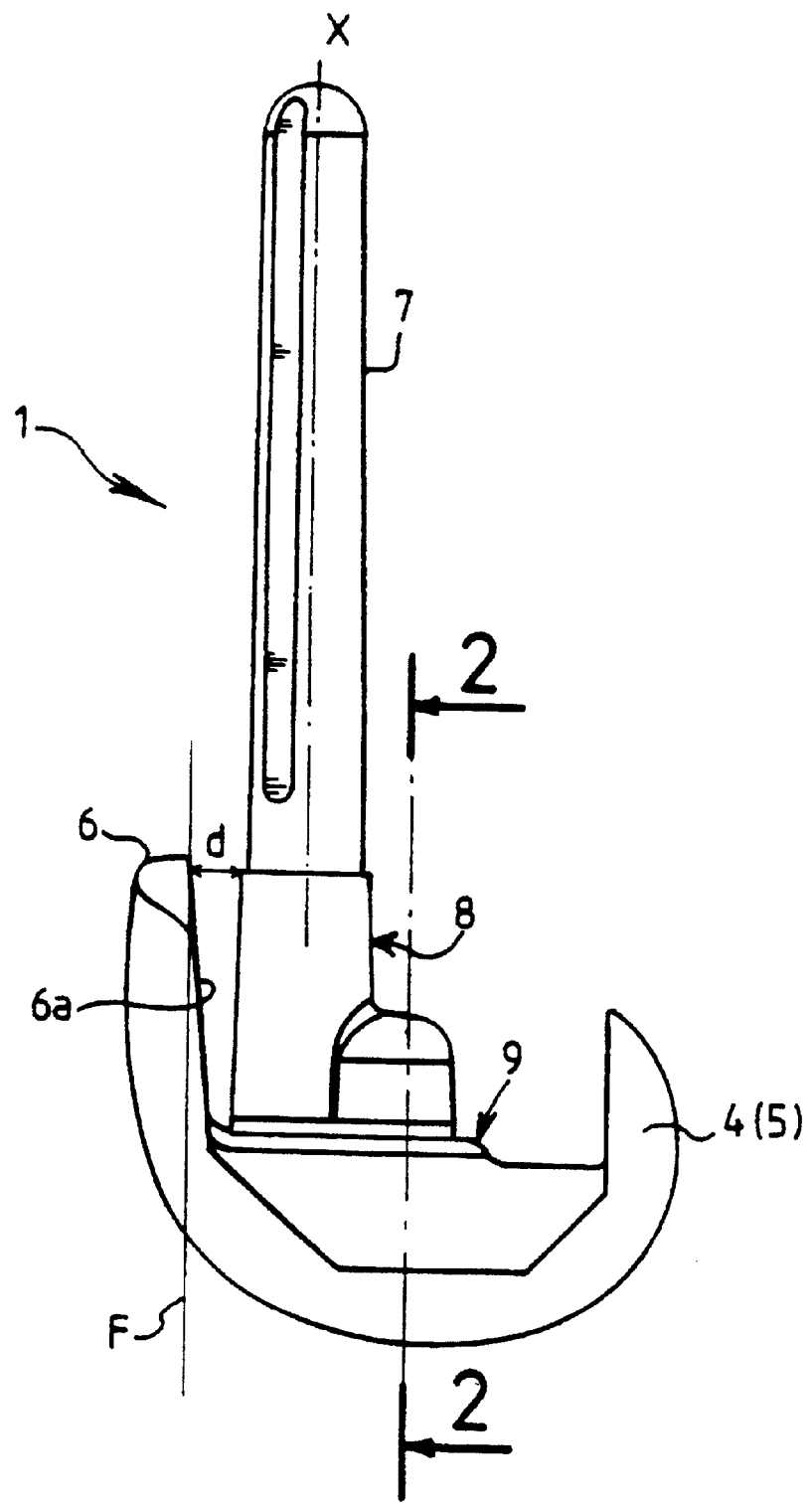
FIG. 1 is a view in side elevation in a sagittal plane of a first embodiment of a femoral implant for knee prosthesis according to the invention.

The femoral implant 1 of FIG. 1 is intended to form part of a knee prosthesis, the associated tibial implant not being shown.

Figure 2:
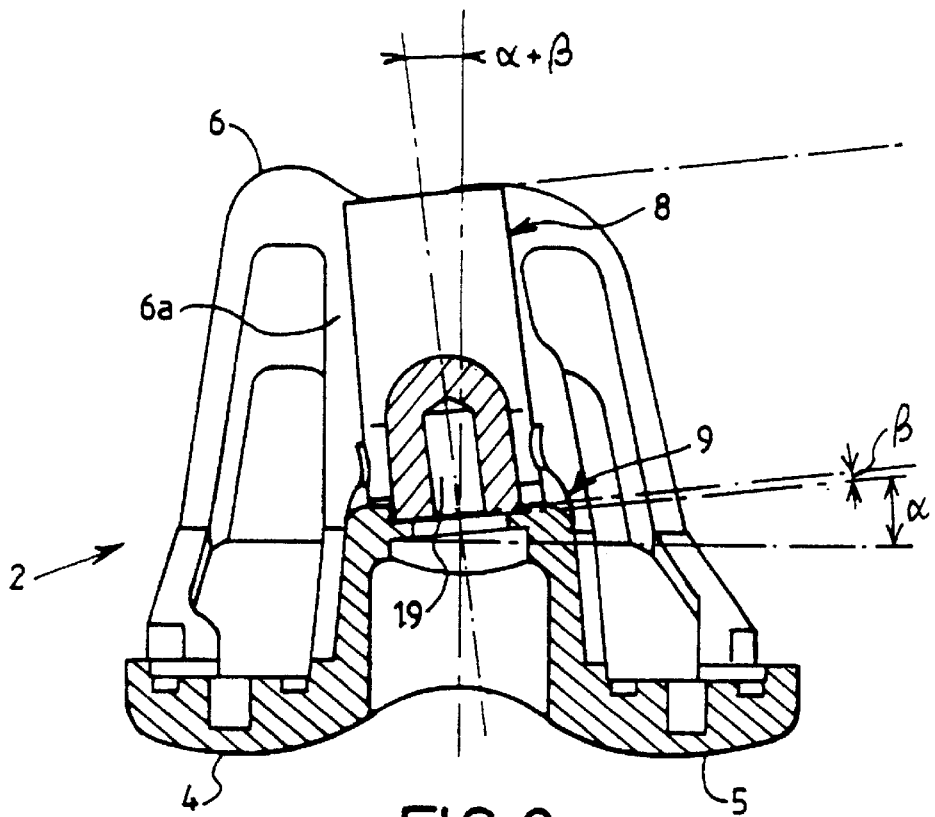
FIG. 2 is a view in partial section along 2/2 of the femoral implant of FIG. 1 without the pre-stem, showing a femoral implant for a left knee corresponding to FIG. 1.
Figure 3:
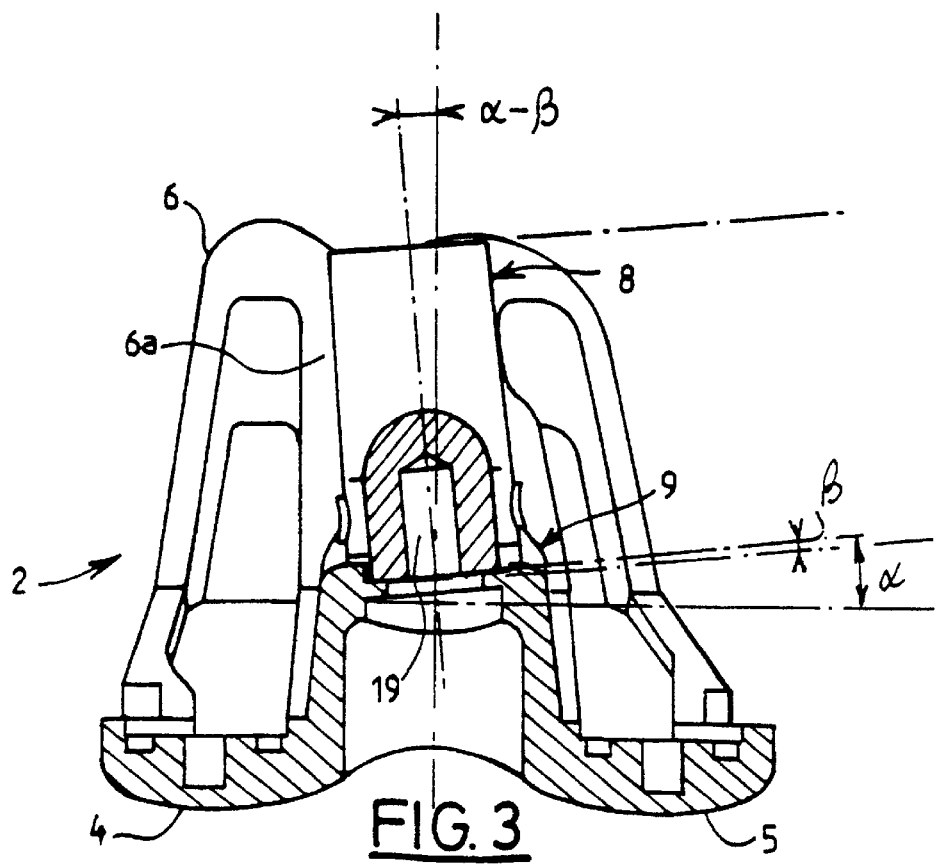
FIG. 3 is a view similar to FIG. 2 showing a different valgus angle obtained with another pre-stem.

The femoral implant 1 may correspond either to a left knee or to a right knee. FIGS. 2 and 3 show a femoral implant 2 intended for a left knee and FIGS. 4 and 5 show a femoral implant 3 intended for a right femur.

The implant 1, 2 or 1, 3 comprises two condyles 4, 5 fast with a trochlea 6, a centro-medullary stem 7 adapted to be introduced in the medullary canal of a femur (not shown) and a "pre-stem" 8 supporting the stem 7. The pre-stem 8 is fixed on a support base 9 arranged between the condyles 4, 5 and is in one piece therewith as well as with the trochlea 6.

Figure 2A:
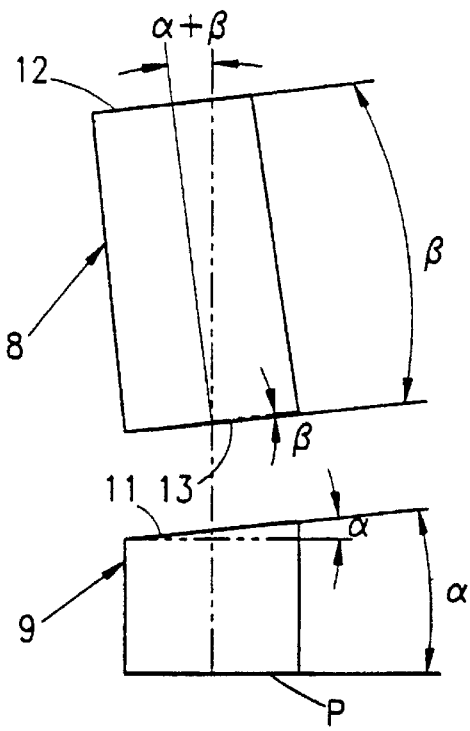
FIGS. 2A and 2B are schematic part elevational views of the base of the implant and of the pre-stem illustrating the manner in which the angle of inclination of the surface of the base and the angle between the opposite faces of the pre-stem can be added to orient a centro-medullary stem in valgus as shown in FIG. 2.

The proximal face 11 of the base 9, on which the pre-stem 8 bears, is planar (FIGS. 2A to 3B) and forms in the frontal plane an angle $\alpha$ with the horizontal plane P, for example 6° (FIG. 2A).

Figure 2B:
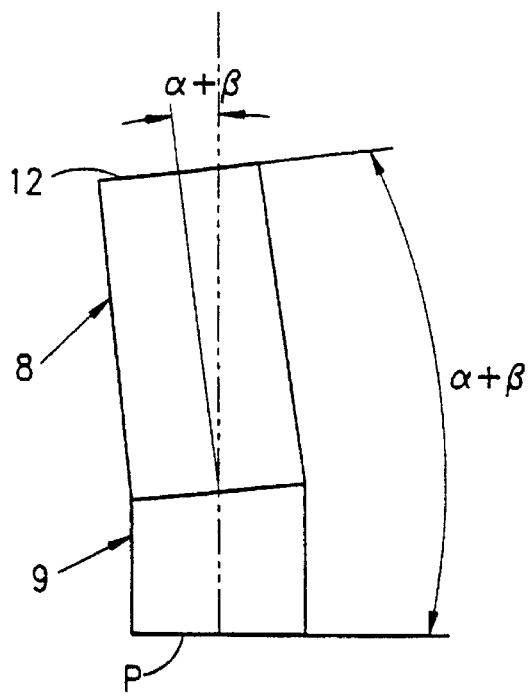

The pre-stem 8 (FIGS. 2, 2A and 2B) presents opposite plane faces 12, 13, proximal and distal respectively, in respective contact with the distal end of the stem 7 and with the surface 11 of the base 9. The opposite plane faces 12, 13 define therebetween a predetermined angle $\beta$, for example of 1°, these faces 12, 13 being divergent towards the right in FIGS. 2A and 2B.

The angle between the proximal face 12 of the pre-stem 8 and the horizontal plane P is equal to $\alpha+\beta$, corresponding to a femoral valgus angle $\alpha+\beta$.

If for example, $\alpha=6°$ and $\beta=1°$, the femoral valgus angle obtained $\alpha+\beta=7°$, which is the case for the femoral implant of FIG. 2 intended for a left femur.

Figure 3A:
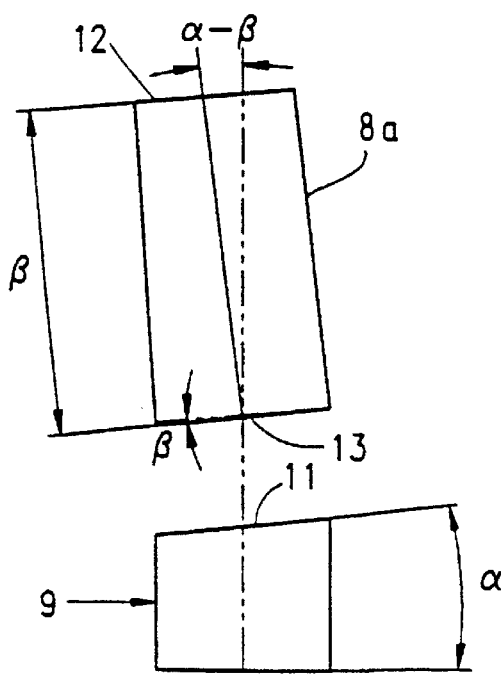
FIGS. 3A and 3B are diagrams similar to FIGS. 2A and 2B illustrating the manner in which a valgus angle different from that of FIGS. 2A and 2B may be obtained with the same pre-stem by orienting it differently.

The pre-stem 8a (FIGS. 3A and 3B) has a distal face 13 inclined by an angle $\beta$ of FIG. 2A with respect to its proximal face 12. The angle between the proximal face 12 and the horizontal plane P is $\alpha-\beta$, viz. a femoral valgus angle of 5° for $\alpha=6°$ and $\beta=1°$, the angle $\beta$ being subtracted from angle $\alpha$.

Figure 3B:
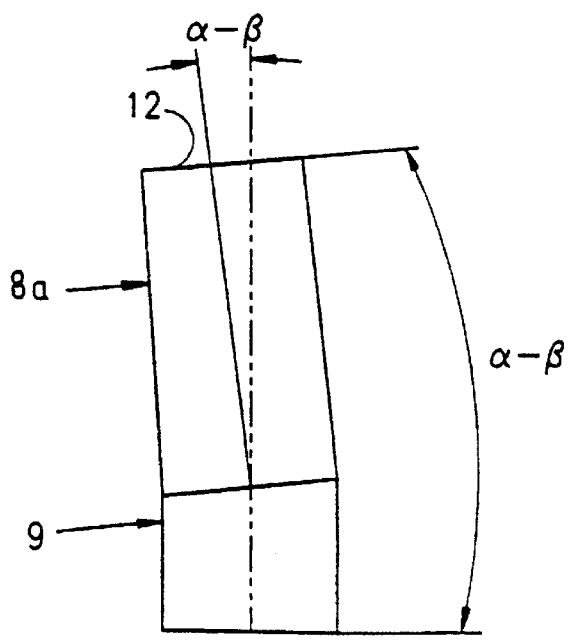

The valgus angle of FIG. 3B corresponds to the one visible in FIG. 3.

For a right femur, the upper plane surface 11 of the base 9 is inclined, in the frontal plane, in the direction opposite that of the surface 11 of the base 9 of an implant 2 for left femur, as shown in FIGS. 4, 5 and 5A to 5B.

This surface 11 may form with the horizontal plane P the same angle $\alpha$ as before and, similarly, the opposite face 12, 12 of the pre-stem 8b, 8d form therebetween an angle $\pm\beta$.

Figure 5B:
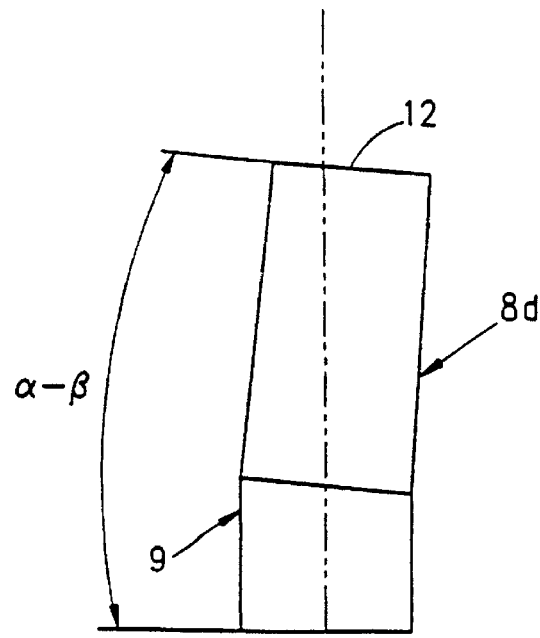

In the case of the pre-stem 8b of angle $+\beta$, the angles $\alpha$ and $\beta$ are added, while with a pre-stem 8d having an angle $-\beta$, the two angles are subtracted (FIGS. 5A and 5B).

A pre-stem 8, 8a, 8b, 8d may, moreover, present a variable profile in the sagittal plane, as illustrated in the two embodiments of FIGS. 6 to 8, 14, 15 and 9 to 11, 16, 17.

The pre-stem 8 (FIGS. 6 to 8 and 14, 15) is constituted by a tubular part 16 of axis XX for receiving the lower end of the stem 7 in a hole 17, and by a widened seat of which the plane lower face 13 abuts the surface 11 of the base 9. In the antero-posterior direction, towards the condyles 4, 5, the seat is widened with respect to the upper part 16 by a boss 18 in which is made a hole 19 intended to receive a securing element (not shown) such as a bolt 50 (FIG. 12) traversing the wall of the base 9.

Thanks to the increased distance x between the axis of the bolt for securing in the hole 19 and the frontal plane F of the trochlea 6, the femoro-patellar surface 60 for abutment of the patella 61 is notably increased. As a result, the patella 61 may remain in abutment on a line of contact of this surface 60 up to an angle of flexion A which may attain about 80 degrees (FIG. 12).

Complementary means for securing the pre-stem 8 to the base 9 are also provided, for example towards and close to the trochlea 6, a stud 21 projecting below the seat and adapted to be introduced in a complementary hole in the base 9. Opposite the anterior wall 6a of the trochlea 6, the wall 21a of the pre-stem 8 is rectilinear. In this way, the pre-stem 8 is profiled so that its upper part 16 and more precisely the upper end of its wall 21a close to the trochlea 6 at a predetermined distance d from the frontal reference plane F passing through the upper end of the trochlea 6 (FIG. 1) and which is the anterior plane, corresponding to the anterior face of the femur.

This distance determines the distance between the axis XX of the pre-stem 7 and the frontal reference plane F, which must be appropriate to the patient's anatomy in order to contribute to a good securing of the pre-stem 7 in the centro-medullary canal and with respect to the anterior cortex.

By way of numerical example, this distance d may for example be 4 mm with the pre-stem 8.

In the embodiment of FIGS. 9 to 11 and 16–17, the pre-stem 22 is profiled so that the distance d with the reference plane F is greater than the corresponding distance with the pre-stem 8 (for example 18.8 mm instead of 14.8 mm). This result is obtained by offsetting the axis XX of the tubular part 16 (which is also that of the stem 7) with respect to the side 21a closest to the trochlea 6, this offset lying in the sagittal plane. To that end, the lower part of the pre-stem 22 presents in the antero-posterior plane an additional boss 23 opposite the trochlea 6 and whose outer face is separated by a distance e2 from the axis XX of the tubular part 16, with e2 greater than e1 (FIG. 6). The corresponding distance d is therefore increased with respect to the distance resulting from the use of the pre-stem 8.

It is thus possible to produce an assembly of orthopaedic material comprising two femoral implants 2, 3, the corresponding stems 7 and a set of a plurality of pre-stems 8, 22 offering a whole range of possibilities for obtaining a predetermined femoral valgus angle and distance d between the upper end of the pre-stem and the frontal reference plane F of the trochlea 6.

For example, two pre-stems can be produced, of which the opposite faces 12, 13 diverge with respect to each other by an angle β, for example of 1°, and of which one presents in the sagittal plane the profile of the pre-stem 8 while the other corresponds to the profile of the pre-stem 22. These two pre-stems are associated with a left or right femoral implant whose base 9 has a surface 11 inclined by a predetermined angle α, for example 6°; the set may comprise two other pre-stems whose opposite faces 12, 13 form therebetween a predetermined angle β which may or may not be the same as for the preceding pre-stems; one of these pre-stems has the profile of the pre-stem 8 and the other that of the pre-stem 22, these two pre-stems being intended for the second, right or left, femoral implant.

Thus, with four pre-stems, there is a total of eight possibilities of use, including four possibilities in valgus and four possibilities in the sagittal plane, each pre-stem leading to a different valgus angle depending on whether it is used on a left or right implant.

This high number of possibilities with a low number of pre-stems despite the asymmetry of the pre-stems in the sagittal plane, which prevents turning thereof through 180 degrees, is due in particular to the arrangement, on the base 9 for supporting the pre-stem, of a face 11 inclined on the horizontal by the angle α. In the absence of such an inclined face, four copies of the pre-stem would be necessary for two different valgus angles and two right and left implants, said inclined face thus enabling this number to be divided by two.

In addition to these advantages, the implant according to the invention ensures an increased bearing zone 60 for the patella 61 thanks to the spacing between the element 50 for securing the pre-stem (8, 22) and the trochlea 6, which increases the life of the patella.

The invention is not limited to the embodiments described and may cover various alternative embodiments. For example, it is obvious that the pre-stem can present in the sagittal plane a profile which is different from those shown. The angles α and β may vary substantially in order to allow femoral valgus angles to be obtained which are appropriate for the anatomical cases which may present themselves.

What is claimed is:

1. A femoral implant of a knee prosthesis, comprising:
   two condyles;
   a support base between the two condyles;
   a centro-medullary stem;
   a pre-stem having a first surface connected to a first planar surface of said support base and a second surface connected to said centro-medullary stem,
   wherein said first planar surface of said support base is inclined with respect to a horizontal plane by a first angle, and
   wherein said first and second surfaces define a second angle there between,
   wherein, said pre-stem is in a first position, a first valgus angle is formed between said second surface and said horizontal plane, when said pre-stem is in a second position, a second valgus angle different from said first valgus angle is formed between said second surface and said horizontal plane.

2. A femoral implant of a knee prosthesis, comprising:
   two condyles integral with a trochlea, said trochlea having a femora-patella surface;
   a support base between the condyles;
   a centro-medullary stem; and
   a pre-stem connected between a surface of said support base and said centro-medullary stem, wherein
   a) said surface of said base receiving the pre-stem is planar and is inclined in a frontal plane by a predetermined angle (α) with respect to a horizontal plane (P),
   b) said pre-stem has opposite distal and proximal plane faces in contact respectively with said surface of said base and with a distal end of said centro-medullary stem and define therebetween, in a frontal plane, a given angle (β) smaller than said predetermined angle (α),
   c) when the pre-stem is fixed on the base, said proximal face forms with the horizontal plane a first valgus angle (α+β) in a first position and second valgus angle (α−β) in a second position,
   d) in a sagittal plane, a profile of the pre-stem has an upper part adjacent to said trochlea at a predetermined distance (d) from a frontal reference plane (F) passing through a proximal end of said trochlea, and
   e) said femoral implant further comprises means for securing said pre-stem to said support base, said means allowing a patella for use with the femoral implant, to slide along a line of contact with the femoral-patella surface up to an angle of flexion (A) of almost 90°.

3. Implant according to claim 2, wherein the pre-stem comprises a tubular part for receiving the stem and a widened seat of which the distal face abuts the support base.

4. Implant according to claim 3, wherein the seat comprises a lateral boss located with respect to the stem towards the condyles and in which a complementary element is housed for securing the pre-stem to the base.

5. An implant according to claim 3, wherein the means for securing are a stud, said stud projecting beneath the seat and structured and arranged in a hole in the support base.

6. An implant according to claim 2, wherein said given angle (β) is substantially smaller than said predetermined angle (α).

7. An implant according to claim 2, wherein said given angle (β) is 1°.

8. Orthopaedic assembly comprising two implants according to claim 7, and a set of a plurality of pre-stems, each having proximal and distal faces forming therebetween a predetermined angle (α), and a particular profile in the sagittal plane, in order to obtain a corresponding number of possibilities of adjustment of the femoral valgus angle (α+β) of the pre-stem and of the stem and of different positionings in a sagittal plane with respect to the frontal reference plane (F).

9. Assembly according to claim 8, comprising four pre-stems:
   two pre-stems of which the proximal and distal faces define therebetween a first angle corresponding to a predetermined valgus angle and which each present a particular profile in the sagittal plane, defining between their upper part for receiving the stem and the reference plane (F) particular respective distances (d);

two other pre-stems of which the opposite faces form therebetween a second angle corresponding to another predetermined valgus angle, and which each present a particular profile in the sagittal plane, defining between its upper part for receiving the stem and the reference plane (F) particular respective distances (d).

10. A femoral implant according to claim 9, wherein the particular respective distance is between 4 and 8 mm.

* * * * *